United States Patent
Yeh et al.

(10) Patent No.: US 12,031,121 B2
(45) Date of Patent: *Jul. 9, 2024

(54) SYSTEMS AND METHODS FOR CULTIVATING ALGAE

(71) Applicant: UNIVERSITY OF SOUTH FLORIDA, Tampa, FL (US)

(72) Inventors: Daniel H. Yeh, Tampa, FL (US); Ivy Lea Cormier Drexler, St. Petersburg, FL (US); Melanie Pickett, Tampa, FL (US); David Fulcher, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/959,263

(22) Filed: Oct. 3, 2022

(65) Prior Publication Data

US 2023/0033254 A1 Feb. 2, 2023

Related U.S. Application Data

(62) Division of application No. 15/350,657, filed on Nov. 14, 2016, now Pat. No. 11,459,535.

(60) Provisional application No. 62/255,044, filed on Nov. 13, 2015.

(51) Int. Cl.
| | | |
|---|---|---|
| C12N 1/12 | (2006.01) | |
| C12M 1/00 | (2006.01) | |
| C12M 1/34 | (2006.01) | |
| C12M 1/36 | (2006.01) | |

(52) U.S. Cl.
CPC .............. *C12N 1/12* (2013.01); *C12M 23/22* (2013.01); *C12M 23/50* (2013.01); *C12M 29/04* (2013.01); *C12M 29/20* (2013.01); *C12M 31/08* (2013.01); *C12M 41/32* (2013.01); *C12M 41/40* (2013.01); *C12M 41/46* (2013.01); *C12M 41/48* (2013.01); *C12M 47/02* (2013.01)

(58) Field of Classification Search
None
See application file for complete search history.

(56) References Cited

U.S. PATENT DOCUMENTS

| | | | | |
|---|---|---|---|---|
| 4,868,123 A | * | 9/1989 | Berson | ............ C12M 23/06 435/286.2 |
| 8,033,047 B2 | | 10/2011 | Rasmussen et al. | |
| 8,399,239 B2 | | 3/2013 | Zhang et al. | |
| 8,642,326 B1 | * | 2/2014 | Schaefer | ............ C12M 21/02 435/257.1 |
| 2009/0130706 A1 | * | 5/2009 | Berzin | ............ C12M 23/06 435/257.1 |
| 2009/0137025 A1 | | 5/2009 | Stephens et al. | |
| 2011/0266215 A1 | * | 11/2011 | Robinson | ............ C02F 1/30 210/602 |
| 2012/0115210 A1 | | 5/2012 | Winters et al. | |
| 2012/0135109 A1 | | 5/2012 | Paeschke et al. | |
| 2013/0232866 A1 | | 9/2013 | Licamele et al. | |
| 2016/0075981 A1 | | 3/2016 | Lee et al. | |
| 2018/0010082 A1 | | 1/2018 | Jaques et al. | |

OTHER PUBLICATIONS

Barros, et al., "Harvesting Techniques applied to microalgae: A review", Renewable and Sustainable Energy Reviews 41, 1489-1500, 2015.

Honda, et al., "Carbon dioxide capture and nutrients removal utilizing treated sewage by concentrated microalgae cultivation in a membrane photobioreactor," Bioresource Technology 125 (2012), pp. 59-64.

Lee, et al., "Fabric-Hydrogel Composite Membranes for Culturing Microalgae in Semipermeable Membrane-Based Photo bioreactors", Polymer Chemistry, Journal of Polymer Science, 54, 108-114, 2016.

* cited by examiner

*Primary Examiner* — Nghi V Nguyen
(74) *Attorney, Agent, or Firm* — Quarles & Brady LLP

(57) ABSTRACT

In one embodiment, an algae cultivation system includes a basin that contains a liquid and a photobioreactor at least partially immersed in the liquid of the basin, the photobioreactor comprising a closed container including multiple panels that together define an interior space in which algae can be cultivated, at least one of the panels being transparent, the photobioreactor further comprising an inflatable float associated with the container that can be filled with a gas to change one or both of the position and orientation of the container within the liquid.

13 Claims, 4 Drawing Sheets

SYSTEMS AND METHODS FOR CULTIVATING ALGAE

CROSS-REFERENCE TO RELATED APPLICATION

This application claims priority to U.S. Provisional Application Ser. No. 62/255,044, filed Nov. 13, 2015, which is hereby incorporated by reference herein in its entirety.

NOTICE OF GOVERNMENT-SPONSORED RESEARCH

This invention was made with Government support under Grant Number 1236746, awarded by the National Science Foundation. The Government has certain rights to the invention.

BACKGROUND

Algae are increasingly recognized as a renewable source of biofuel, but also have many other commercially valuable applications, such as pharmaceuticals, animal/fish feed, and fertilizers. However, there remain many problems in the large-scale production of algae, which hinder its economic competitiveness with other biofuel crops.

Algae are typically small in size (2-30 μm) and are cultivated in relatively dilute concentrations (generally less than 0.5 g dry biomass L-1), which makes harvesting and dewatering microalgal cultures particularly problematic and expensive. External inputs, such as nutrients, freshwater, and gases, also add a substantial environmental and economic burden. Wastewater, on the other hand, is a free source of nutrients, water, and carbon dioxide, if utilized in algae production, could improve the economics and environmental footprint of large-scale algae production. However, utilizing wastewater may increase the chances of introducing predators, grazers, and invasive species to a microalgal culture, which can lead to algal culture collapse. As a case in point, open raceway ponds are easily contaminated by environmental contaminants (e.g., bacteria, fungi, and rotifers). Although synthetic growth media can be sterilized before it is added to a closed algal culture, this can add substantial cost to production.

From the above discussion, it can be appreciated that it would be desirable to have an alternative system and method with which algae can be cultivated, harvested, and dewatered.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative system and method with which algae can be cultivated, harvested, and dewatered. Examples of such systems and methods are disclosed herein. The systems and methods include one or more photobioreactors that comprise selectively inflatable floats that can be used to control the position and/or orientation of the photobioreactor when it is immersed in a pool of liquid. In some embodiments, the photobioreactors include porous membrane filters that enable the passive transport of constituents (i.e., nutrients and gases) from a growth medium while still maintaining a physical barrier for potential competitors/predators/grazers or contaminants, such as endemic wastewater species, airborne pathogens, or bacteria/protozoans/metazoans, contained in the growth medium. In such an embodiment, the floats can be inflated to raise the position of the photobioreactor in the pool to dewater the algae that has been cultivated within the photobioreactor. In other embodiments, the floats can be inflated to raise one side of the photobioreactor so as to tilt the photobioreactor to facilitate harvesting of the algae that has been cultivated within the photobioreactor.

In the following disclosure, various specific embodiments are described. It is to be understood that those embodiments are example implementations of the disclosed inventions and that alternative embodiments are possible. All such embodiments are intended to fall within the scope of this disclosure.

This disclosure addresses issues of cultivation, harvesting, dewatering, and predator/grazer invasion in the production of algae. The disclosed systems and methods can be used with various types of growth media. The nutrients and carbon dioxide in the growth media, such as wastewater, can be used as a feedstock for algae production. As noted above, the photobioreactors in which the algae is cultivated can be manipulated using selectively inflatable floats to change the position and/or orientation of the photobioreactor for purposes of dewatering and/or harvesting. In some embodiments, the floats can be inflated using photosynthetic gas (namely oxygen) generated by the algae cultivation process. In other embodiments, the floats can be inflated using another gas source.

During photosynthesis, algae consume either dissolved carbon dioxide (an autotrophic reaction), dissolved organic carbon (a heterotrophic reaction), or a combination thereof (a mixotrophic reaction), and produce oxygen as a byproduct. Because oxygen has a lower water solubility than either carbon dioxide or dissolved organic carbon, it partitions readily into the gas phase. If such photosynthesis occurs in a photobioreactor in which gas-phase oxygen is not allowed to escape into the atmosphere (such as a closed bioreactor), then the accumulated oxygen in the headspace will generate a pressure in the headspace of the photobioreactor.

Figure 1:
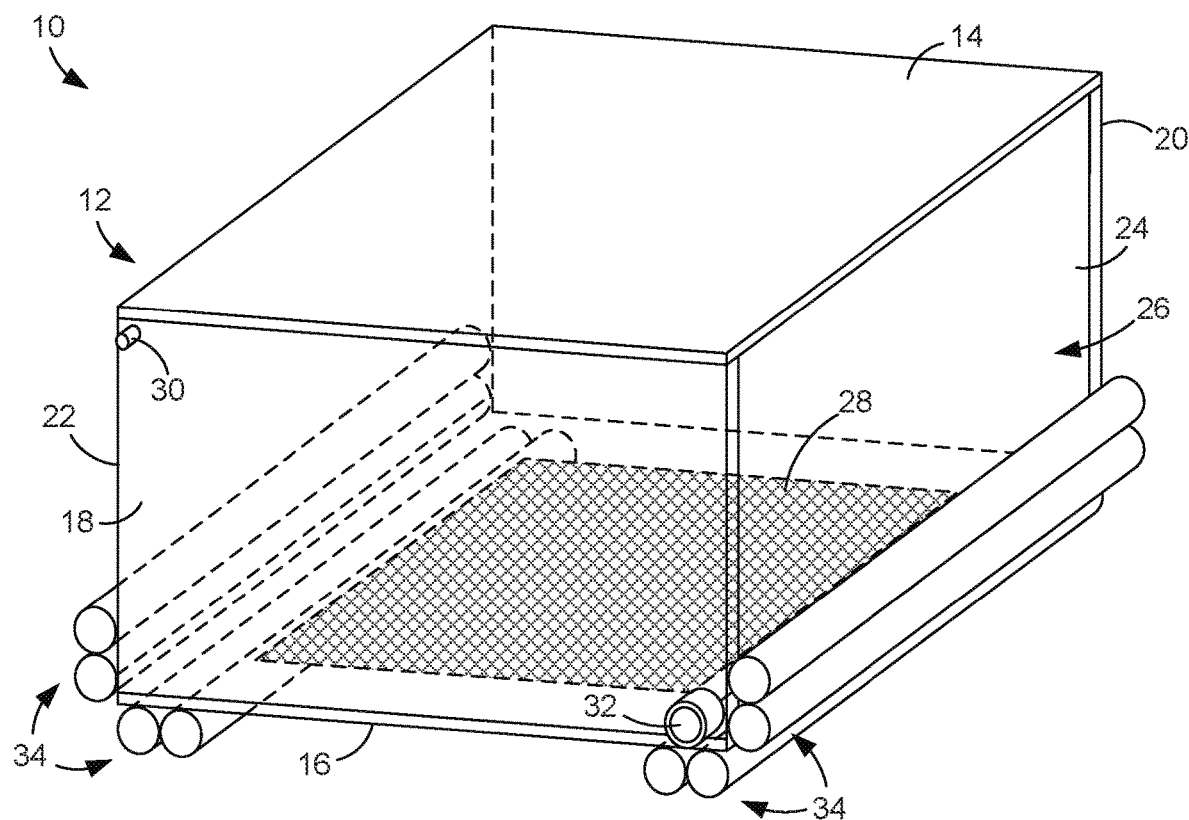
FIG. 1 is a perspective view of a first embodiment of a photobioreactor configured to enable controlled dewatering of algae cultivated within the photobioreactor.
Figure 2:
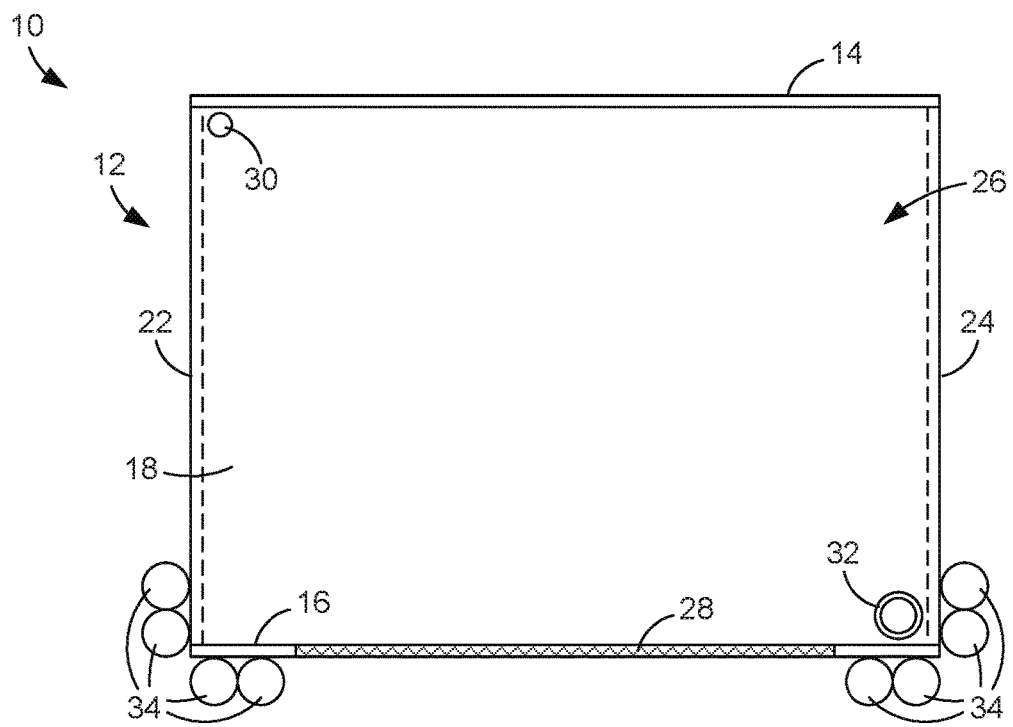
FIG. 2 is an end view of the photobioreactor of FIG. 1.

FIGS. 1 and 2 illustrate an embodiment of a photobioreactor 10 that can be incorporated into an existing or future algae cultivation system, stormwater pond, waste stabilization lagoon, wastewater reactor (e.g., aeration basin or settling clarifier), or other wastewater structure or waterway. As shown in these figures, the photobioreactor 10 is configured as a generally rectangular container 12 that includes multiple generally planar wall panels. In the example of FIGS. 1 and 2, these panels include a top panel 14, a bottom panel 16, a first end panel 18, a second end panel 20, a first side panel 22, and a second side panel 24. Each of these panels 14-24 can be generally perpendicular to each other to form an orthogonal rectangular box that defines an interior space 26. While an orthogonal rectangular box has been described and illustrated, it is noted that substantially any shape could be used, including three-dimensional polygons, cylinders, or hexagons. The particular shape that is used is not critical and may be influenced by various factors, such as the nature of the structure in which the photobioreactor 10 is to be used.

The size of the container 12 can be selected to suit the particular application in which it will be used. In some embodiments, however, the container 12 can have a length of approximately 1 to 10 m, a width of approximately 1 to 3 m, and a height of approximately 0.1 to 1 m, and the interior space 26 can have a volume of approximately 0.1 to 30 m$^3$. The container 12 can be transparent, or at least translucent, in which case the panels 14-24 can be made of a material that enables light, particularly sunlight, to easily pass through the panels. In some embodiments, the panels 14-24 are made of a clear polymeric material, such as an acrylic or polycarbonate material. Each of the panels 14-24 can be sealed along their shared edges to prevent ingress or egress of fluids. In some embodiments, one or more of the panels 14-24, such as the top panel 14, can be opened or removed from the container 12 to facilitate seeding of the container 12 and/or harvesting of algae from the container.

The container 12 further includes a porous membrane filter 28. In the embodiment of FIGS. 1 and 2, this porous membrane filter 28 is incorporated into the bottom panel 16. In particular, the bottom panel 16 comprises an opening that the porous membrane filter 28 covers. This membrane filter 28 enables water, gases (e.g., carbon dioxide and oxygen), and nutrients (e.g., nitrogen and phosphorus) to pass into the interior space 26 of the container 12, but prevents entry of contaminants and other unwanted components of the growth media into the space.

The parameters of the membrane filter 28, such as material, thickness, porosity, and permeability, can influence how the system functions and its selection is influenced by the overall goals of the system operation. Polymeric materials with a backing or cloth textile material having a pore size in the range of approximately 0.01 to 0.2 μm (20 to 350 kDa) may be preferable because they are durable and effective in precluding entry of potential biological contaminants. However, other membrane filter types could be utilized for projects with goals different than optimizing biomass productivity or culture protection. For example, if predation is less of a concern than the capital cost of the porous membrane filter photobioreactor infrastructure, a membrane filter with a pore size of 1 μm or greater could be used to reduce costs. However, with large pore sizes, seed culture may escape and predatory organisms may invade until a biological coating layer (biofilm) forms on the membrane filter surface. The membrane filter parameters may also influence constituent transport, which in turn affect overall productivity and/or algae metabolism. For example, if a project goal is to induce lipid production by restricting nitrogen, smaller membrane filter pores may be employed to retard the diffusion of nitrogen species across the membrane filter surface. In some embodiments, it is preferable that the pores of the membrane filter 28 are less than approximately 1 μm in size. By way of example, the pores can be in the range of approximately 0.01 to 0.2 μm (~20 to 350 kDa). In some cases, the membrane filter 28 can comprise an ultrafiltration membrane filter that forms part of a removable membrane filter cartridge that seals to the bottom panel 16 of the container 12.

With further reference to FIGS. 1 and 2, the container 12 also comprises a gas vent 30 that can be used to release photosynthetic gas generated within the container 12. As illustrated in this figure, the gas vent 30 can be provided in one of the end or side panels 18-24 (panel 18 in FIGS. 1 and 2) near a top end of the panel or in the top panel 14 so as to be located above a water line within the container and in fluid communication with a headspace of the container. As gas builds up within the container 12 due to photosynthetic gas (e.g., oxygen) production that occurs during algae cultivation, the gas can be vented from the container 12. In some embodiments, this gas can be used to control the position and/or orientation of the container 12 within a pool of liquid, such as liquid growth media. In other embodiments, the gas can be collected and used for other purposes. For example, photosynthetic oxygen may be used in other aerobic processes (e.g., wastewater treatment, aquaculture). As described below, one or more gas control valves can be used to direct the gas for one or more particular end uses.

The container 12 can further include an algae extraction port 32 that can be opened to facilitate removal of the algae that has been cultivated within the container. This algae can be pumped out of the container 12 through the extraction port 32 to harvest the algae.

With further reference to FIGS. 1 and 2, the photobioreactor 10 also includes one or more inflatable floats 34 that can be used to control the position and/or orientation of the photobioreactor 10 within a pool of liquid for purposes of dewatering and/or harvesting of the algae that has been cultivated within the photobioreactor. In the illustrated embodiment, these floats 34 comprise elongated cylindrical elements that are attached to the lower portions of the photobioreactor 10. In particular, the float elements are mounted to the bottom panel 16 and the side panels 22, 24 near bottom (side) corners of the container 12. While a particular configuration and mounting scheme has been described and illustrated, it will be appreciated that other configurations and mounting schemes can be used and provide the same functionality. As noted above, the floats 34 can be inflated using gas generated by the algae cultivation process. Alternatively, the floats 34 can be inflated using another gas source. In some embodiments, the float elements comprise flexible bags that can be inflated by a relatively low-pressure gas flow.

Figure 3A:
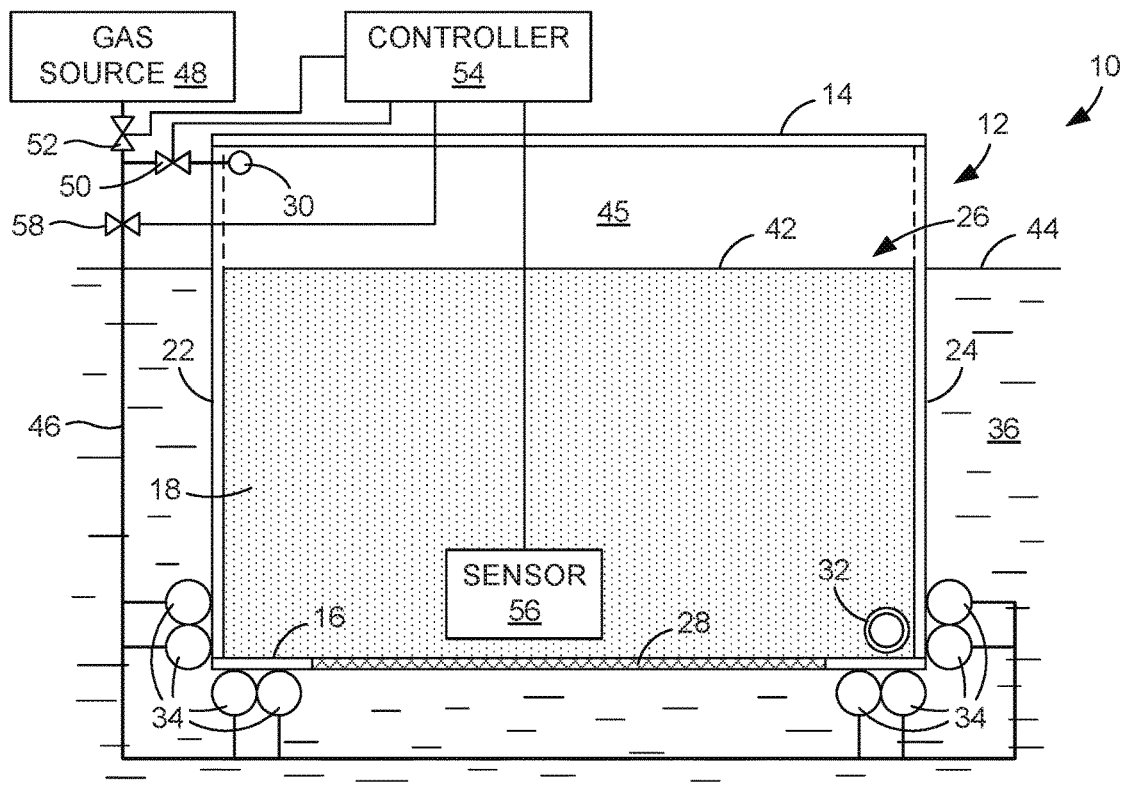
FIGS. 3A and 3B are end views of the photobioreactor of FIG. 1 and illustrate controlled dewatering of algae within the photobioreactor.
Figure 3B:
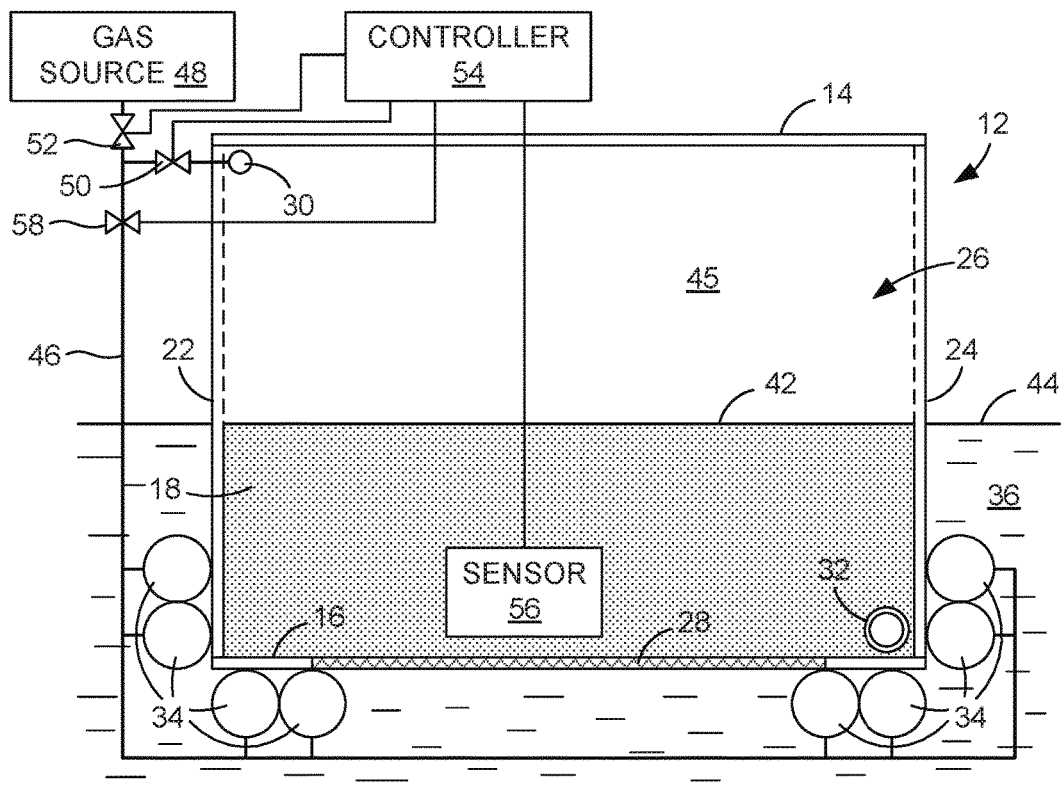
Figure 4:
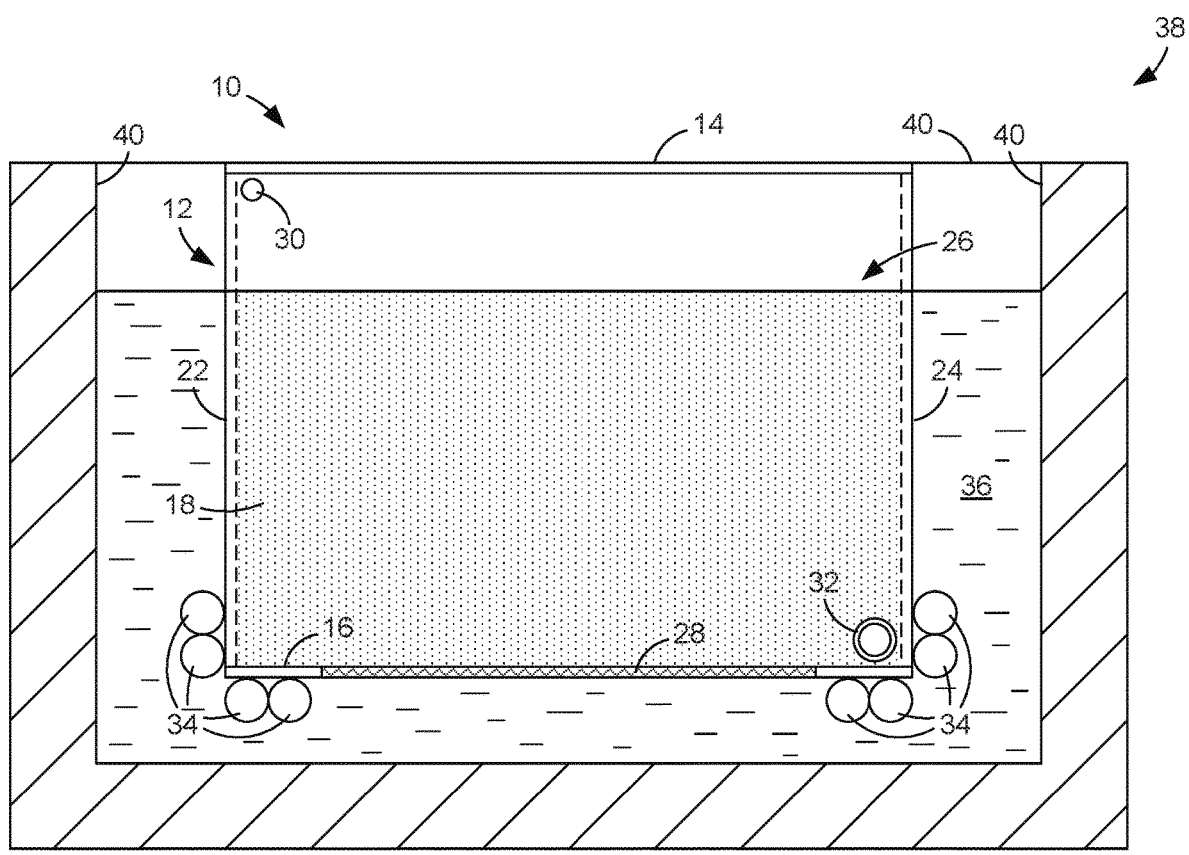
FIG. 4 is an end view of an open-topped growth media reactor in which a photobioreactor is immersed.

FIGS. 3A and 3B illustrate an example of operation of the photobioreactor 10. In this example, the inflatable floats 34 are used to dewater the algae that has been cultivated within the photobioreactor. As shown in these figures, the photobioreactor container 12 is partially immersed in a water-based growth media 36, which may comprise wastewater. As an example, growth media can be contained in an outdoor, open-topped basin, such as a growth media reactor, or a wastewater plant reactor or clarifier. FIG. 4 illustrates an example of an outdoor, open-topped growth media reactor 38 that contains growth media 36. One or more containers 12 can be positioned within the reactor 38 such that the top panels 14 of the containers are positioned above the surface of the growth media 36 while the other panels are completely or at least partially immersed in the media. The depth at which the containers 12 are immersed can vary the volume of algae culture that is produced. The containers 12 can either float within the growth media 36 using the floats 34 (e.g., with the floats in a partially inflated state) and/or can be tethered to walls 40 of the reactor 38 with tethers (not shown). When the containers 12 are correctly positioned within the reactor 38, the growth media 36 within the reactor can pass through the porous membrane filters 28 of the containers 12 and enter their interior spaces 26. Prior to immersion in the growth media 36, the photobioreactor containers 12 can be seeded with algal cells of the target algae species that is to be cultivated. When the containers 12 are exposed to light, particularly sunlight, the algae will then grow within the containers.

In an initial state shown in FIG. 3A, in which algae is beginning to grow, water fills the container to a point at which the surface 42 of the water within the container 12 is generally equal to the surface 44 of the growth media 36 in which the container is immersed. As the algae grows, photosynthetic gas, such as oxygen, is generated by growth of the algae and rises to a headspace 45 within the container 12 above the surface 42 of the water within the container. This gas can flow out of the gas vent 30 and through a gas line 46 that extends to the inflatable floats 34 such that the gas can inflate (or further inflate) the floats.

As depicted in FIG. 3B, as the floats 34 fill (or further fill) with gas, the container 12 is raised in height relative to the growth media 36. As the container 12 rises, water within the container exits the container to equalize the water level within the container with that of the growth media 36. As a consequence of this equalization, the algae within the container 12 is concentrated (i.e., dewatered) at the bottom of the container. This algae may be in the form of an algal slurry that can be removed from the container 12 during harvesting, for example, via the algae extraction port 32.

In some embodiments, this above-described process can be self-sustaining. Specifically, as a greater and greater amount of algae is produced, a greater and greater amount of gas is produced and, therefore, the higher and higher the container is raised. Accordingly, as a mass of algae is produced that is suitable for harvesting, the algae is automatically concentrated such that the algae, when harvested, has been significantly dewatered, thereby reducing the costs normally associated with producing a crop of algae.

Alternatively or additionally, inflation of the floats 34 can be achieved using another source of gas. For example, a gas source 48, such as a source of pressurized air or a gas compressor or pump, can be used to selectively inflate the floats 34 when desired. In order to enable alternate inflation of the floats 34 using the photosynthetic gases and gas from the separate gas source 48, the photobioreactor 10 can further include gas control valves 50 and 52 that can be used to control which source is used for inflation. For example, if the floats 34 are to be inflated using the photosynthetic gas, the valve 50 can be opened and the valve 52 can be closed. If the floats 34 are instead to be inflated using the separate gas source 48, the valve 50 can be closed and the valve 52 can be opened. These valves 50, 52 can be manually actuated or electrically actuated. In the latter case, the valves 50, 52 can comprise, for example, solenoid valves.

The valves 50, 52 can, in some embodiments, be automatically opened or closed at appropriate times. For example, valves 50, 52 can be actuated by a controller 54, such as a computer or microprocessor-based controller, in response to a signal received by a sensor 56 that is configured to sense a parameter indicative of the algae reaching a state at which dewatering should be performed. By way of example, the sensor 56 can comprise an optical sensor, a density sensor, a pressure sensor, a temperature sensor, a chlorophyll sensor, a nutrient/ion sensor, a dissolved gas sensor, a turbidity sensor, or combinations thereof. In other embodiments, the sensor 56 can be located in the headspace of the photobioreactor and comprise a pressure sensor and or a temperature sensor.

In some embodiments, the photobioreactor 10 can further include a gas release valve 58 provided along the gas line 46 that, when opened, can release gas that has inflated the floats 34 for purposes of periodically clearing the membrane filter 28 without the need to remove the container 12 from the growth media 36. Specifically, if the photobioreactor 10 has been raised up by the floats 34, the gas release valve 58 can be suddenly opened to enable the gas in the floats to escape, which results in the container 12 sinking and water flowing through the porous membrane filter 28 and back into the interior space 26. This water flow may clear algae from the inside surface of the membrane filter 28 that would otherwise clog the membrane filter and inhibit the passage of water, nutrients, and gas into the container 12.

Figure 5A:
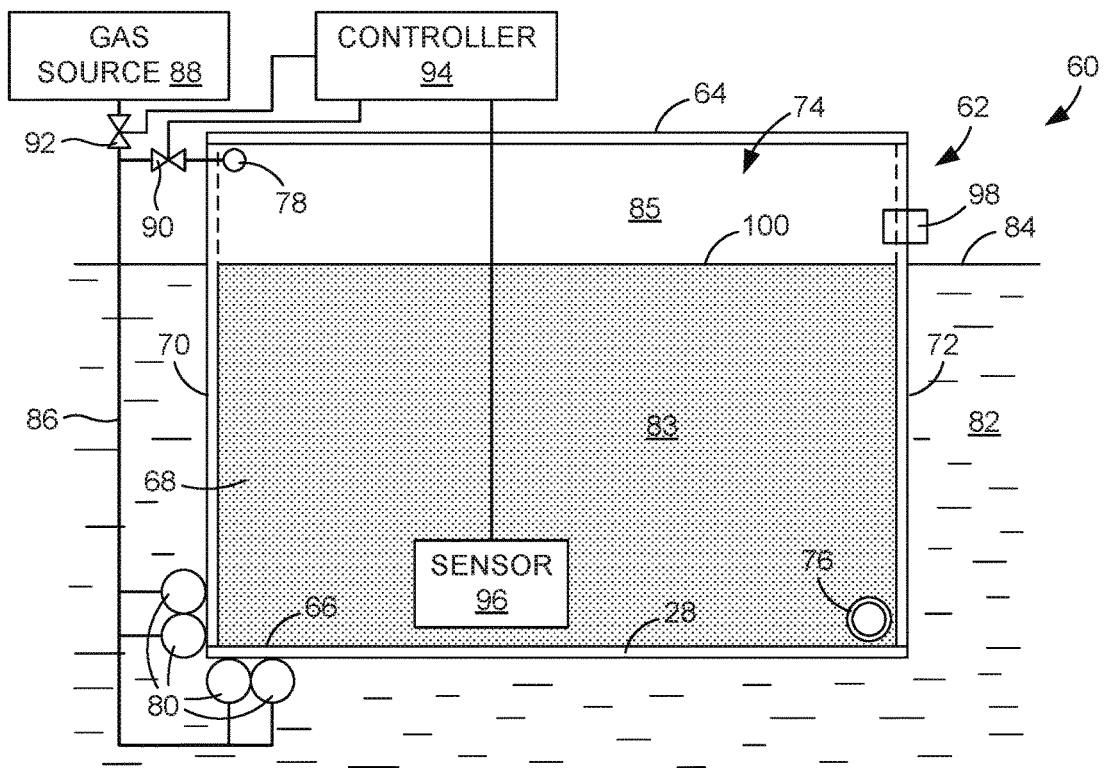
FIGS. 5A and 5B are end views of a second embodiment of a photobioreactor and illustrate controlled tilting of the photobioreactor to facilitate harvesting of algae cultivated within the photobioreactor.
Figure 5B:
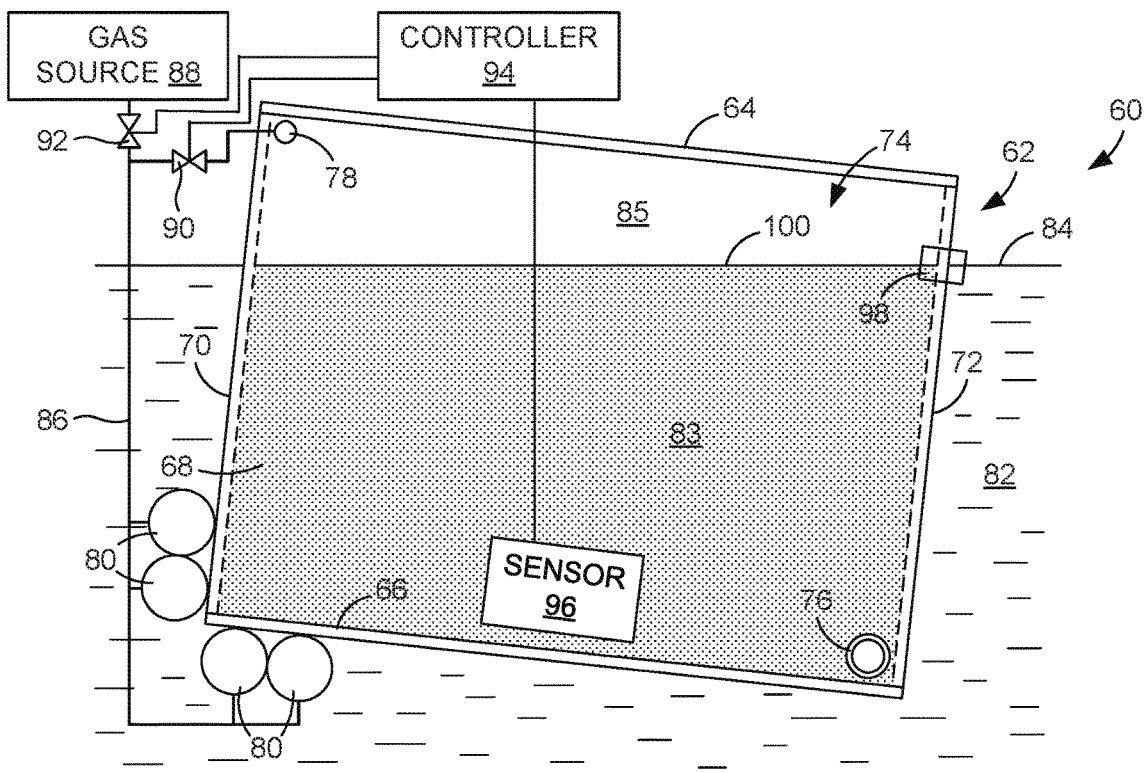

In addition to facilitating dewatering, floats of the type described above can also be used to facilitate harvesting. FIGS. 5A and 5B illustrate an example of this. In particular, these figures illustrate a photobioreactor 60 that includes many of the features of the photobioreactor 10 shown in FIGS. 1 and 2. The photobioreactor 60 is also configured as a generally rectangular container 62 that includes multiple generally planar wall panels, including a top panel 64, a bottom panel 66, a first end panel 68, a second end panel (not visible), a first side panel 70, and a second side panel 72. Like the container 12, the container 62 forms a box that defines an interior space 74, which can, for example, have a volume of approximately 0.1 to 30 $m^3$.

The container 62 can be transparent, or at least translucent, in which case the panels are made of a material that enables light, particularly sunlight, to easily pass through the panels. In some embodiments, the panels are made of a clear polymeric material, such as an acrylic material. Each of the panels can be sealed along their shared edges to prevent ingress or egress of fluids. As with the container 12, one or more of the panels, such as the top panel 64, can be opened or removed from the container 62 to facilitate seeding of the container and harvesting of algae from the container. In addition, however, the container 62 includes an algae extraction port 76 that can be opened to facilitate removal of the algae that has been cultivated within the container 62. This algae can be pumped out of the container 62 through the extraction port 76. In the illustrated embodiment, the container 62 does not include a porous membrane filter such that the container is completely sealed and liquid cannot enter or exit the container once it has been closed. It is noted, however, that in other embodiments, such a filter can be provided, if desired.

Like the photobioreactor 10, the photobioreactor 60 comprises a gas vent 78 that can be used to vent gas generated within the container 62. This gas can be used to tilt the container 12 to facilitate algae harvesting. In particular, the gas can be used to inflate one or more inflatable floats 80 that are provided on only one side of the container 62. As shown in FIGS. 5A and 5B, the floats 80 can be mounted to the bottom panel 66 and the side panels 70, 72 near a bottom (side) corner of the container 62.

As shown in FIGS. 5A and 5B, the photobioreactor container 12 is partially immersed in a liquid 82, such as water. In an initial state shown in FIG. 5A, algae is beginning to grow and the container 62 is generally level with the horizontal plane. Although the level of the growth media 83 inside the container 62 is shown as being equal with the surface 84 of the liquid 82 in which the container is immersed, it is noted that it need not be so. As the algae continues to grow within the container 62, photosynthetic gas, such as oxygen, is generated and rises to a headspace 85 within the container 62. This gas can flow out of the gas vent 78 and through a gas line 86 that extends to the inflatable floats 80 such that the gas can inflate the floats.

Referring to FIG. 5B, as the floats 80 fill with this gas, the container 62 is tipped or tilted to accumulate algae near the algae evacuation port 76. Accordingly, the algae can be more easily removed from the container 62. As above, this process can be self-regulating. Specifically, as a greater and greater amount of algae is produced, a greater and greater amount of gas is produced and, therefore, the more and more the container is tilted. Accordingly, as a mass of algae is produced that is suitable for harvesting, the algae is automatically shifted toward the algae extraction port 76.

As before, the inflation of the floats 80 can be achieved using another source of gas. For example, a gas source 88, such as a source of pressurized air, can be used to selectively inflate the floats 80 when desired. In order to enable inflation of the floats 80 alternately using the photosynthetic gases and gas from the separate gas source 88, the photobioreactor 60 can further include gas control valves 90 and 92 that can be used to control which source is used for inflation. For example, if the floats 80 are to be inflated using the photosynthetic gas, the valve 90 can be opened and the valve 92 can be closed. If the floats 80 are instead to be inflated using the separate gas source 88, the valve 90 can be closed and the valve 92 can be opened. These valves 90, 92 can be manually actuated or electrically actuated. In the latter case, the valves 90, 92 can comprise, for example, solenoid valves.

The valves 90, 92 can, in some embodiments, be automatically opened or closed at appropriate times. For example, valves 90, 92 can be actuated by a controller 94, such as a computer or microprocessor-based controller, in response to a signal received by a sensor 96 that is configured to sense a parameter indicative of the algae reaching a state at which dewatering should be performed. By way of example, the sensor 96 can comprise an optical sensor, a density sensor, or a turbidity sensor.

In addition to removing algae via the algae extraction port 76, algae can be removed by opening one of the panels (e.g., the top panel 64) to access the interior space of the container 62. For example, a skimmer could be used to remove floating algae. In other embodiments, the photobioreactor 60 can be configured to facilitate extraction of algae from the surface of the liquid within the photobioreactor without opening the photobioreactor. As shown in FIGS. 5A and 5B, the container 62 can further include a supplemental algae extraction port 98 positioned near the top of the container that can be used for this purpose. As indicated in FIG. 5B, when the container 62 is tilted to an appropriate degree, the surface 100 of the liquid within the container will be level with the port 98 so as to enable a precise volume of algae to pour from the container. An internal skimmer (not shown) may also be employed to drive the algae to the port 98. In some embodiments, multiple ports positioned at different heights along the container 62 can be used to collect algae of different densities due to age, oil content, size, diurnal differences in cell structure/size, or other phylogenetic differences. For example, some species (or cells of the same species under different metabolic stages) may be carried to the surface 100 whereas others would settle to the bottom of the container 62. Utilizing these buoyancy differences enable the selective harvest of algae with specific traits. Selective placement of the extraction ports can be used to prevent washout of immature cells and/or encourage harvest of only species with certain characteristics.

In some embodiments, venting of gas from the container 62 can be controlled to enable selective rupturing of algal cells. For example, the gas control valve 90 can be closed to build pressure within the headspace 85 of the container. Because the container 62 is closed, this pressure would pressurize the algal cells within the container. If the gas control valve 90 is suddenly opened and the gas is permitted to escape, the concomitant pressure drop within the container 62 may cause algal cells to rupture, causing oil to be released that floats to the surface 100 of the growth media 83 within the container. This oil can then be extracted using the algae extraction port 98. Notably, temperature may also induce such rupture as the temperature and pressure within the container 62 may increase during daytime hours and decrease during nighttime hours.

What is claimed is:

1. An algae cultivation system comprising:
   a basin that contains a liquid; and
   a photobioreactor at least partially immersed in the liquid of the basin, the photobioreactor comprising a container including multiple panels that together define an interior space in which algae can be cultivated to produce photosynthetic gas, at least one of the panels being transparent, the photobioreactor further comprising multiple inflatable floats associated with the container, wherein each of the multiple inflatable floats is in fluid communication with the interior space and can be selectively filled with the photosynthetic gas from the interior space to change one or both of the position and orientation of the container within the liquid,
   wherein the multiple inflatable floats are mounted to opposite sides of the container and, when inflated, raise the height of the container in the liquid,
   wherein the photobioreactor further comprises a porous membrane filter that enables water, gases, and nutrients contained within the liquid of the basin to pass into the interior space of the container but prevents contaminants contained within the liquid from passing into the interior space and wherein raising of the height of the container enables water to exit the container through the filter to dewater the algae.

2. The system of claim 1, wherein the basin is an outdoor, open-top growth media reactor.

3. The system of claim 1, wherein the container comprises multiple transparent panels.

4. The system of claim 1, wherein at least one of the multiple inflatable floats comprises an inflatable bag.

5. The system of claim 1, wherein at least one of the multiple inflatable floats is mounted to one side of the container and, when inflated, tilts the container in the liquid.

6. The system of claim 1, wherein the container further comprises a gas vent through which photosynthetic gas produced by algae growth within the container can escape the container and a gas line that connects the gas vent to at least one of the multiple inflatable floats such that gas that escapes the container travels through the gas line and inflates the inflatable float.

7. The system of claim 1, wherein the photobioreactor further comprises an algae extraction port through which algae can be removed from a bottom of the container.

8. A photobioreactor adapted for immersion in a liquid contained within a basin, the photobioreactor comprising:
   a container including multiple panels that together define an interior space in which algae can be cultivated to produce photosynthetic gas in the interior space, at least one of the panels being transparent;

multiple inflatable floats mounted to the container that can be filled with the photosynthetic gas from the interior space to change one or both of the position and orientation of the container within the liquid; and a gas vent incorporated into the container that fluidly connects the interior space to the inflatable float and enables the photosynthetic gas produced by algae growth within the container to be selectively directed to at least one of the multiple inflatable floats, wherein the multiple inflatable floats are mounted to opposite sides of the container and, when inflated, raise the height of the container in the liquid, wherein the photobioreactor further comprises a porous membrane filter that enables water, gases, and nutrients contained within the liquid of the basin to pass into the interior space of the container but prevents contaminants contained within the liquid from passing into the interior space and wherein raising of the height of the container enables water to exit the container through the filter to dewater the algae.

9. The photobioreactor of claim 8, wherein the photobioreactor comprises multiple transparent panels.

10. The photobioreactor of claim 8, wherein at least one of the multiple inflatable floats comprises an inflatable bag.

11. The photobioreactor of claim 8, wherein at least one of the multiple inflatable floats is mounted to one side of the container and, when inflated, tilts the container in the liquid.

12. The photobioreactor of claim 8, wherein the container further comprises a gas line that connects the gas vent to at least one of the multiple inflatable floats such that gas that escapes the container travels through the gas line and inflates the inflatable float.

13. The photobioreactor of claim 8, wherein the photobioreactor further comprises an algae extraction port through which algae can be removed from a bottom of the container.

* * * * *